(12) United States Patent
Deverre et al.

(10) Patent No.: US 9,192,756 B2
(45) Date of Patent: Nov. 24, 2015

(54) DEVICE INTENDED TO BREAK AT LEAST ONE CLOSURE ELEMENT LOCATED INSIDE A FLEXIBLE TUBE

(75) Inventors: Frederic Deverre, Montpellier (FR); Pierre Eloi Bontinck, Lille (FR); Arnaud Chavatte, Isbergues (FR); Toni Schroeder, Dreieich (DE)

(73) Assignee: Maco Pharma, Mouvaux (FR)

(*) Notice: Subject to any disclaimer, the term of this patent is extended or adjusted under 35 U.S.C. 154(b) by 120 days.

(21) Appl. No.: 13/994,028

(22) PCT Filed: Dec. 14, 2011

(86) PCT No.: PCT/FR2011/052992
§ 371 (c)(1),
(2), (4) Date: Jun. 13, 2013

(87) PCT Pub. No.: WO2012/080664
PCT Pub. Date: Jun. 21, 2012

(65) Prior Publication Data
US 2013/0256576 A1    Oct. 3, 2013

(30) Foreign Application Priority Data
Dec. 14, 2010    (FR) .................................. 10 04885

(51) Int. Cl.
*F16K 17/14*    (2006.01)
*A61M 39/22*    (2006.01)

(52) U.S. Cl.
CPC ....... *A61M 39/221* (2013.01); *A61M 2039/222* (2013.01); *A61M 2209/04* (2013.01)

(58) Field of Classification Search
CPC .................... A61M 39/221; A61M 2039/222; A61M 2209/04; Y10T 137/1632
USPC ............... 137/68.11; 251/349, 350; 604/244, 604/167.01, 167.03, 403; 225/103; 81/3.2, 81/3.4
See application file for complete search history.

(56) References Cited

U.S. PATENT DOCUMENTS

| 2,659,253 | A | * | 11/1953 | Myrick | 225/93 |
| 4,340,049 | A | * | 7/1982 | Munsch | 604/29 |
| 4,386,622 | A | * | 6/1983 | Munsch | 137/1 |
| 4,410,026 | A | * | 10/1983 | Boggs et al. | 383/60 |
| 4,586,928 | A | * | 5/1986 | Barnes et al. | 604/408 |
| 5,267,586 | A | * | 12/1993 | Jankavaara | 137/565.12 |
| 6,132,413 | A | * | 10/2000 | Mathias et al. | 604/403 |

(Continued)

FOREIGN PATENT DOCUMENTS

WO    WO 2004058046 A2 *    7/2004

*Primary Examiner* — Craig Schneider
*Assistant Examiner* — Minh Le
(74) *Attorney, Agent, or Firm* — IP Attorneys Group, LLC

(57) ABSTRACT

The invention relates to a device intended to break at least one closure element located inside a flexible tube, said closure element having a first part and a second part, said parts being separated by a weakening zone, it being possible to break said weakening zone in order to enable fluid to flow inside said flexible tube, said device comprising an assembly for holding said flexible tube, said assembly comprising a fixed element provided with a first housing intended to hold a first portion of said flexible tube, and a mobile element provided with a second housing intended to hold a second portion of said flexible tube, the two housings being aligned along a center line defining a neutral position of the mobile element, said device comprising a member for moving the mobile element to either side of its neutral position so as to be able to break the weakening zone of the closure element.

19 Claims, 10 Drawing Sheets

(56) References Cited

U.S. PATENT DOCUMENTS

| | | | |
|---|---|---|---|
| 7,490,723 B2* | 2/2009 | Levisman | 206/368 |
| 7,597,226 B2* | 10/2009 | Starr | 225/96.5 |
| 2009/0120505 A1* | 5/2009 | Brierton et al. | 137/68.11 |
| 2010/0132512 A1* | 6/2010 | Bucciaglia et al. | 81/3.2 |
| 2011/0004144 A1* | 1/2011 | Beiriger et al. | 604/6.11 |
| 2011/0192204 A1* | 8/2011 | Steinhilber et al. | 72/17.3 |
| 2014/0263529 A1* | 9/2014 | Stonig | 225/103 |

* cited by examiner

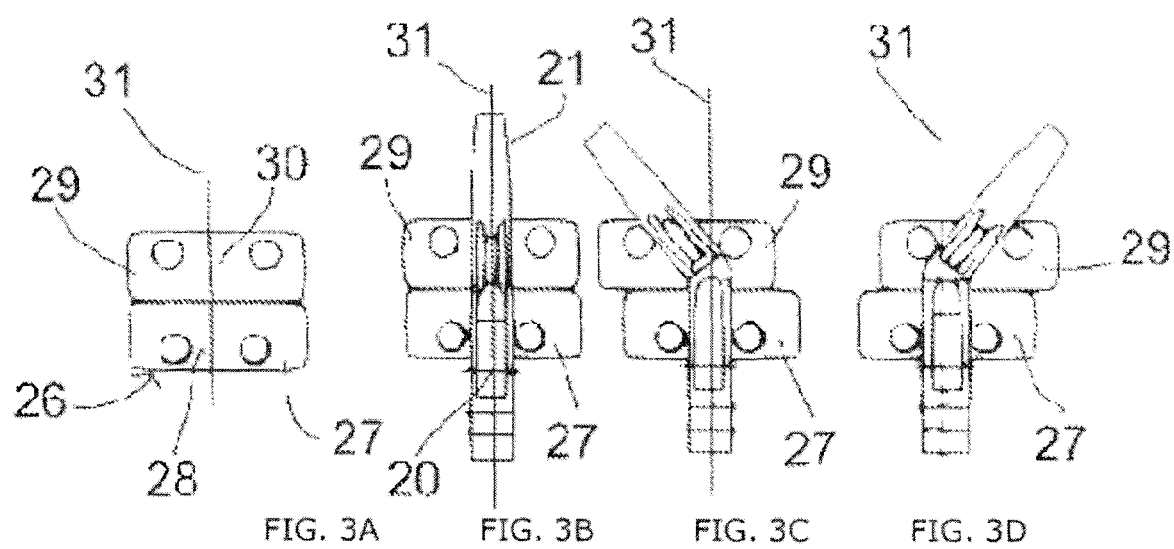

DEVICE INTENDED TO BREAK AT LEAST ONE CLOSURE ELEMENT LOCATED INSIDE A FLEXIBLE TUBE

CROSS REFERENCE TO RELATED APPLICATIONS

This application is a national phase filing of pending International Application No. PCT/FR2011/052992 filed on Dec. 14, 2011 titled "DEVICE INTENDED TO BREAK AT LEAST ONE CLOSURE ELEMENT LOCATED INSIDE A FLEXIBLE TUBE", which claims priority of French Patent Application No. 1004885 filed on Dec. 14, 2010 entitled "Dispositif destiné à rompre au moins un élément de fermeture disposé à l'intérieur d'un tube souple". The contents of the above-identified Applications are relied upon and incorporated herein by reference in their entirety.

The invention relates to a device intended to break a closure element arranged inside a flexible tube, as well as an apparatus comprising such a device and a method for breaking a closure element using such a device.

It typically applies in the field of transfusion and perfusion with the breakage of closure elements placed inside a flexible tube of a bag system. These closure elements are generally designated as open-circuits.

Open-circuits are valve devices housed inside a flexible tube, preventing the flow of fluid until the manual breaking of the open-circuit when a blood product or other solution must pass inside this tube. An example of such open-circuits is described in WO-93/1 7734.

Most transfusion centres treat nearly 8,000 blood donations per day. Breaking these open-circuits, during blood collection and separation of blood components, is a repetitive and restrictive step that generates musculoskeletal disorders in the medical staff. The most common pathologies are tendonitis, carpal tunnel syndrome or tenosynovitis.

WO-2004/058046 proposes to automate the opening of open-circuits by supplying a retractable hook integrated into a blood treatment apparatus. The breakage of the open-circuit is carried out by a linear or rotating movement that folds the open-circuit on only one side. This manipulation does not make it possible to ensure the complete breakage of the open-circuit.

WO-2010/065396 proposes a portable device for opening breakable open-circuits comprising two hooks, mobile in opposite directions in relation to one another, and enabling a back-and-forth movement in order to break the open-circuit. This type of device has the disadvantage of moving the bag during the breaking of the open-circuit. When the bag contains various blood components separated by centrifugation, the breaking of the open-circuit with such a device can cause the re-mixing of the blood components, which is not desirable.

The invention aims to overcome these various problems by proposing in particular a device, which is particularly simple to carry out and use. This device also makes it possible to reduce the time of labour, and to provide efficient and reproducible breakage of all types of open-circuits, and to reduce the operations on centrifuged bags which can alter the separation. Finally, the integration of this device into an apparatus for treating a biological fluid makes it possible to minimise the risk of errors linked with handling bag systems.

To this end, and according to a first aspect, the invention relates to a device intended to break at least one closure element arranged inside a flexible tube, said closure element comprising a first part and a second part separated by a weakening zone, said weakening zone able to be broken in order to enable fluid to flow inside said flexible tube, said device comprising an assembly for holding said flexible tube, said assembly comprising a fixed element provided with a first housing intended to hold a first portion of said flexible tube, and a mobile element provided with a second housing intended to hold a second portion of said flexible tube, the two housings being aligned along a centre line defining a neutral position of the mobile element, said device comprising a member for moving the mobile element to either side of its neutral position, in such a way as to be able to break the weakening zone of the closure element when the flexible tube is placed in the assembly for holding.

According to a second aspect, the invention relates to a method for breaking a closure element using a device according to the first aspect, comprising the steps of:
  placing the flexible tube comprising the closure element in the assembly for holding of said device with the weakening zone arranged between the fixed element and the mobile element,
  actuating the member for moving the mobile element on either side of its neutral position in such a way as to break the weakening zone of the closure element.

BRIEF DESCRIPTION OF THE DRAWINGS

FIGS. 3A-3D show diagrammatical views of an assembly embodiment for use in the bag system depicted in FIG. 1.

FIG. 1 shows a bag system 1 used for collecting blood and separating blood components in transfusion. This bag system 1 is typically comprised of a bag 2 for collecting the blood connected to a blood sampling needle 3 by the intermediary of a first flexible tube 4. A needle protector 5 is placed on the first flexible tube 4 and is intended to cover the needle 3 at the end of the blood sample.

Figure 1:
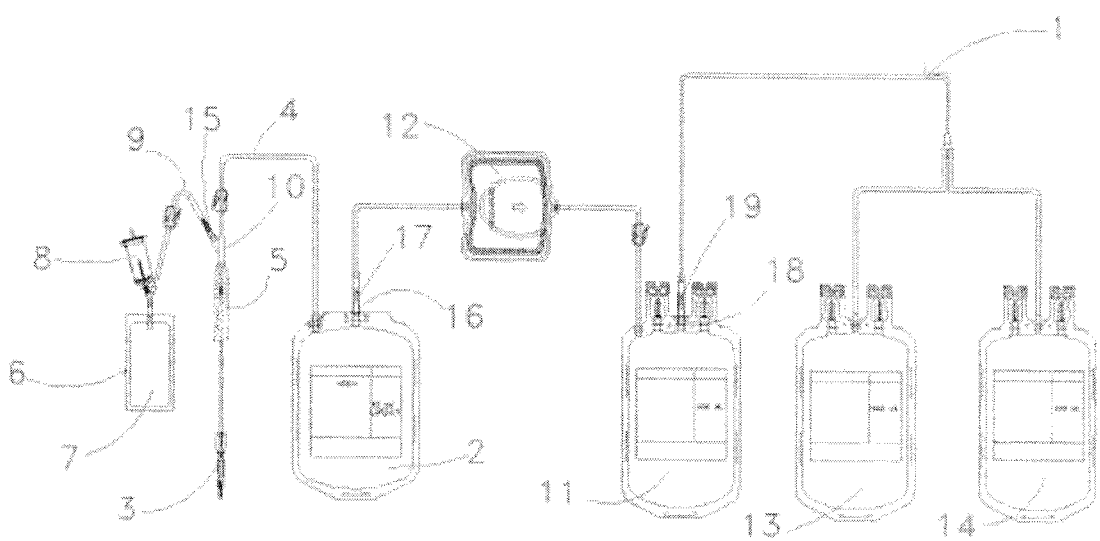
FIG. 1 shows a diagrammatical view of a bag system used for collecting and separating blood components.

A sampling assembly 6 comprising a sampling bag 7 and a device for transferring 8 to a vacuum tube (not shown) is connected to the first flexible tube 4 by the intermediary of a second flexible tube 9. The first and second flexible tubes are connected together by the intermediary of a Y-connector 10. This sampling assembly 6 is used to sample the blood sample in order to carry out analyses.

The collection bag 2 is furthermore connected by the intermediary of a third flexible tube to a primary bag 11. In FIG. 1, a filter 12 for leukodepleting whole blood is arranged on this third flexible tube. The primary bag 11 is intended to collect the filtered blood through the leukodepleting filter 12. The primary bag 11 is in fluid communication with two secondary bags 13, 14 intended to respectively receive the plasma and the packed red blood cells obtained after centrifugation of the primary bag 11 containing the filtered whole blood.

The collection bag 2 comprises an anticoagulant of the ACD (acid citrate dextrose) or CPD (citrate phosphate dextrose) type. In order to prevent the anticoagulant from penetrating into the sampling assembly and distorting the analyses, a first closure element 15 is arranged on the Y-connector 10. Likewise, one of the outlet orifices 16 of the collection bag is provided with a second closure element 17 in order to prevent the anticoagulant from moving into the rest of the bag system 1, in particular during the production of these systems, during the step of sterilisation.

In FIG. 1, a third closure element 18 is arranged on an orifice 19 of the primary bag 11 in order, during the centrifugation of the primary bag 11, to prevent sending on-separated blood into the secondary bags 13, 14.

There are several types of closure elements. Generally and as shown in the FIGS. 2A to 2C, a closure element 20 is arranged inside a flexible tube 21. The closure element comprising a first part 22, designated as base, and a second part 23, designated as pen. These two parts 22, 23 are separated by a weakening zone 24, said weakening zone able to be broken in order to enable fluid to flow inside said flexible tube 21.

In more detail, the first part 22 of the closure element 20 is formed of a hollow cylinder of which the outer diameter substantially corresponds to the inner diameter of said flexible tube 21 wherein the closure element is inserted. As such, the outer diameter of this first part 22 is substantially equal or slightly greater than the inner diameter of the flexible tube 21 as such preventing the passage of the fluid on the sides of the base 22 of the closure element.

The second part 23 of the closure element 20 is formed of a cylinder or of a solid cone. In the flexible tube 21, the fluid can flow around this second part 23. In the FIGS. 2A to 2C, the second part comprises fins 25, facilitating the passage of fluid around the pen 23, after breakage of the weakening zone 24.

Figures 2A, 2B, 2C:
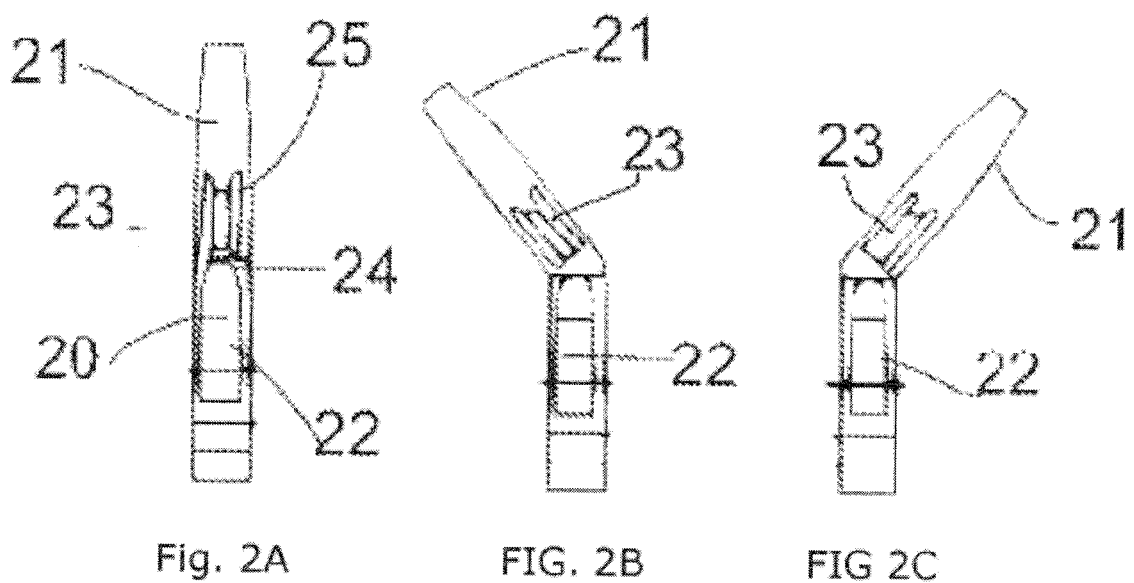
FIGS. 2A-2C show diagrammatical views of a closure element embodiment for use in the bag system depicted in FIG. 1.

In order to enable the fluid to flow, the user manipulates the flexible tube 21 from the exterior in order to fold the second part 23 of the closure element 20 in order to carry out the breaking of the weakening zone 24 and separate the two parts 22, 23 of the closure element (FIGS. 2B and 2C). Once separated, the fluid can flow inside the first part 22 of the closure element.

According to a first aspect, the invention relates to a device intended to break at least one closure element arranged inside a flexible tube.

As described hereinabove, the closure element comprises a first part and a second part separated by a weakening zone, said weakening zone able to be broken in order to enable fluid to flow inside said flexible tube.

As shown in FIGS. 3A to 3D and 4A to 4D, the device comprises an assembly for holding 26 the flexible tube 21 inside of which the closure element 20 is arranged. The assembly 26 comprises a fixed element 27 provided with a first housing 28 intended to hold a first portion of said flexible tube, and a mobile element 29 provided with a second housing 30 intended to hold a second portion of said flexible tube, with the two housings 28, 30 being initially aligned along a centre line 31. In this initial state, the mobile element 29 is said to be in a neutral position wherein the flexible tube 21 can be placed in the assembly for holding 26.

The two fixed and mobile elements 27, 29 are arranged one above the other. The housings 28, 30 are arranged initially to maintain the closure element 20 in its tube 21 in an unbroken state.

Figure 6:
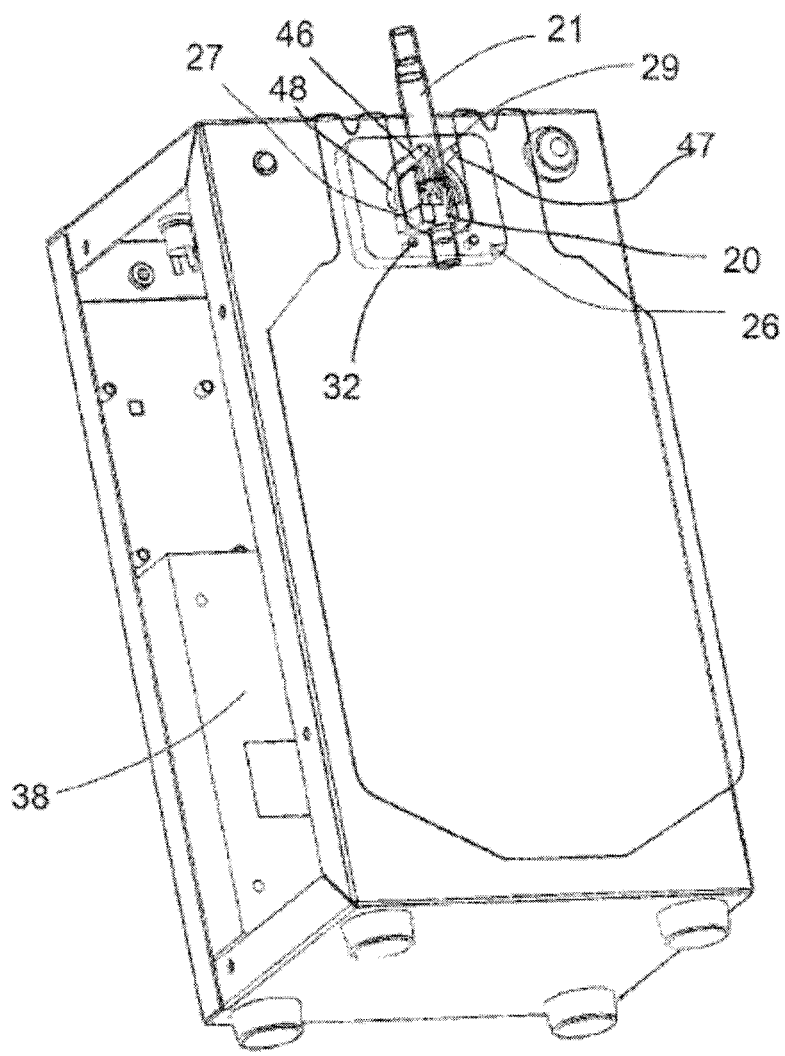
FIG. 6 shows a view of an assembly in use with a bag system as depicted in FIG. 1.
Figure 7:
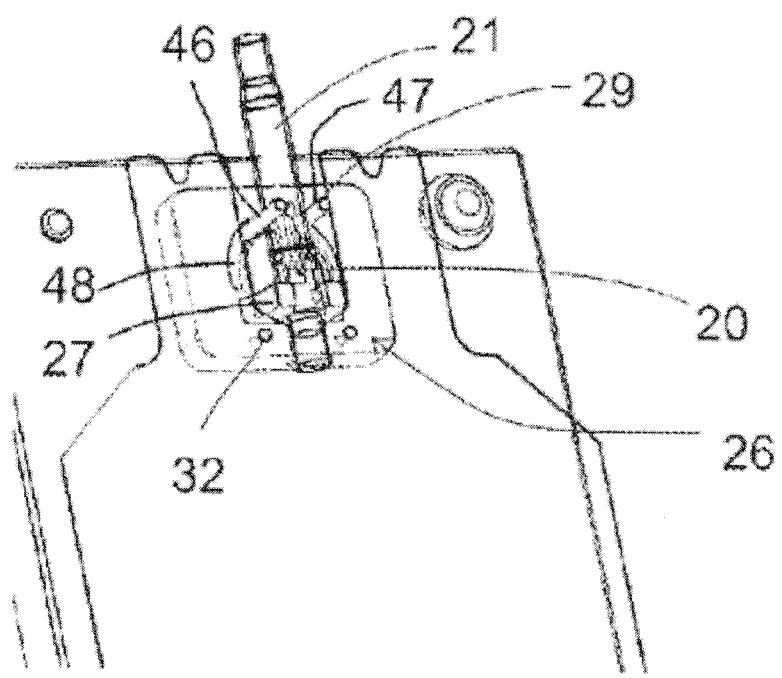
FIG. 7 shows a larger view of the assembly as shown in FIG. 6.

According to an embodiment, at least one of the housings 28 is formed inside a U-shaped groove as shown in FIGS. 6 and 7 for the housing 28 of the fixed element 27.

In order to firmly hold the fixed element 27 during the displacement of the mobile element 29 on one side and the other of the centre line 31, the length of the housing 28 of the fixed element 27 is substantially equal to the length of the fixed element 27.

The housing 30 of the mobile element 29 is comprised of two parallel rods 46, 47 separated by a distance that is substantially equivalent to the outer diameter of the flexible tube 21.

In order to allow for the displacement of the mobile element 29 in relation to the fixed element 27, the assembly for holding comprises a cavity 48 corresponding to the shape of the movement of the mobile element. In FIGS. 6 and 7, the movement of the mobile element is a movement of rotation and the cavity has an arc of circle shape.

Generally, transfusion bags include suspension eyebolts. Rods 32 can be provided on the assembly for holding 26 in order to hold said suspension eyebolts. These rods are arranged on the assembly for holding 26 in such a way that the closure element or elements 20 are directly lodged in the housings 28, 30 provided. This configuration facilitates the setting up of closure elements 20 in the device.

According to another embodiment, at least one of the housings 28 comprises a clamp intended to tighten a portion of the flexible tube 21.

By fixed element is meant an element that is not moved during the breaking of the weakening zone of the closure element. The fixed element can be mobile before or after the steps of breaking.

By mobile element is meant an element that is displaced during the breaking of the weakening zone of the closure element. During the displacement of the mobile element in order to carry out the breaking of the closure element, the fixed element remains immobile.

Figure 5:
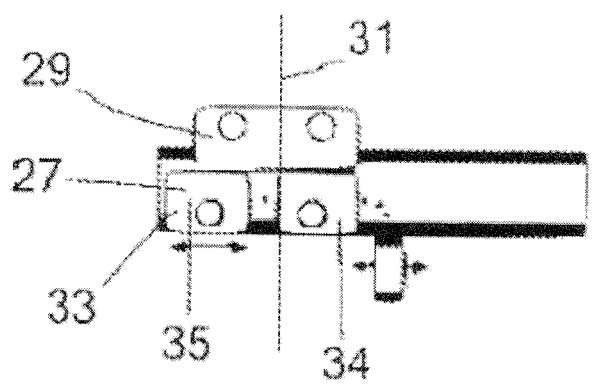
FIG. 5 shows a diagrammatical views of a further assembly embodiment for use in the bag system depicted in FIG. 1.

For example in FIG. 5, the fixed element 27 comprises a clamp 33 formed of two rods 34, 35 of which one 34 is fixed and the other 35 is mobile in linear translation in order to adjust the separation of the two rods 34, 35 to the diameter of the flexible tube 21.

Figures 4A, 4B, 4C, 4D:
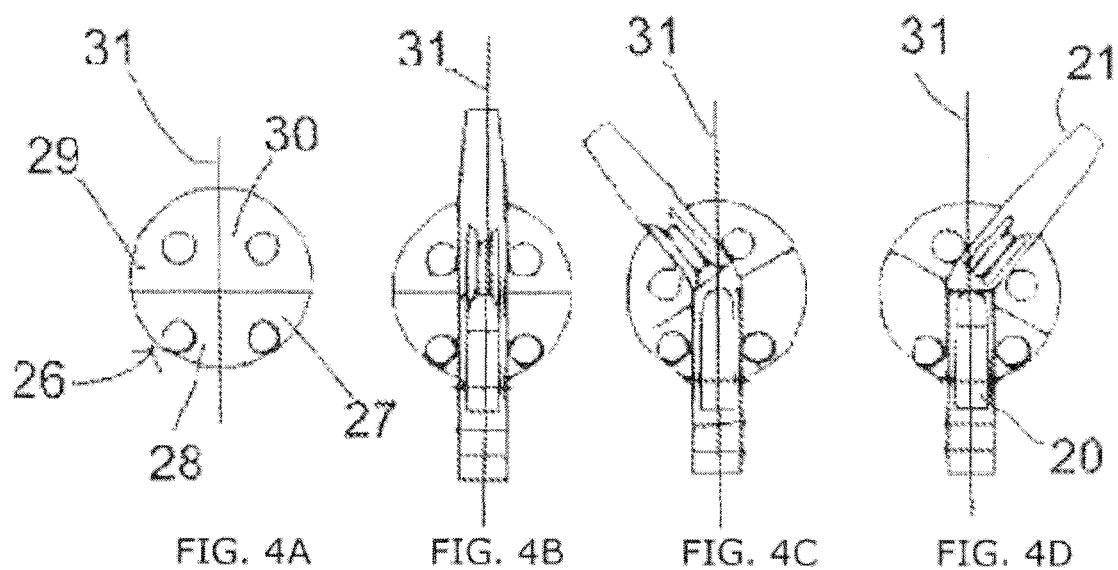
FIGS. 4A-4D show diagrammatical views of another assembly embodiment for use in the bag system depicted in FIG. 1.

The housings 28, 30 of the fixed element 27 and of the mobile element 29 are aligned along a centre line 31. This centre line corresponds substantially to the axis of the flexible tube 21 when it is arranged in the two housings 28, 30. In this initial position with the two housings aligned, the mobile element 29 is said to be in a neutral position. The mobile element 29 being in this initial neutral position, the closure element 20 is in its unbroken state as shown in FIGS. 3B and 4B.

The device comprises a member 36 for moving the mobile element 29 to either side of its neutral position, in such a way as to be able to break the weakening zone 24 of the closure element 20 when the flexible tube 21 is placed in the assembly for holding 26. As such, the mobile element 29 can be moved on either side of the centre line 31, between a position shifted on one side of said line and a position shifted on the other side of said line.

During the use of the breakage device, the mobile element 29 carries out a back-and-forth movement beyond its neutral position, making it possible to effective separate the first and the second part 22, 23 of the closure element 20.

According to a first embodiment, shown in FIGS. 3A to 3D, the mobile element 29 is moved according to a linear movement. The mobile element is then displaced perpendicularly to the centre line 31, towards the right and towards the left, in a back-and-forth movement by passing through the neutral position.

According to a second more advantageous embodiment shown in FIGS. 4A to 4D, the mobile element 29 is moved according to a movement of rotation. In this case, the axis of rotation is perpendicular to the centre line 31.

In order to minimise the force needed to break the weakening zone 24, the axis of rotation of the mobile element 29 passes through the centre line 31.

Advantageously, in order to provide the breaking of the weakening zone 24 of the closure element 20, the movement of rotation of the mobile element 29 is a movement of at least 30°, more preferably of at least 45°, on either side of the centre line 31.

The movement of rotation reduces the risk of tearing or of deformation of the flexible tube in relation to the rectilinear translation movement of the first embodiment.

Figure 8:
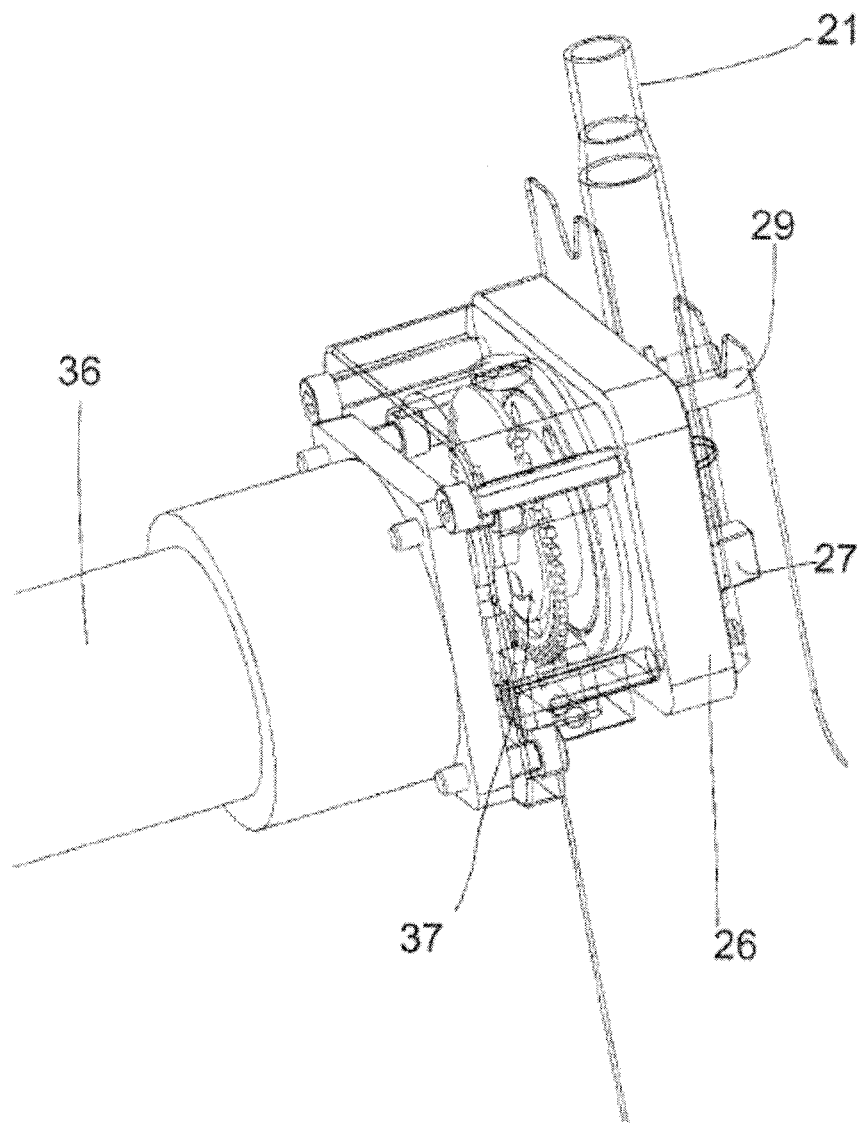
FIG. 8 shows another larger view of the assembly as shown in FIG. 6.
Figure 9:
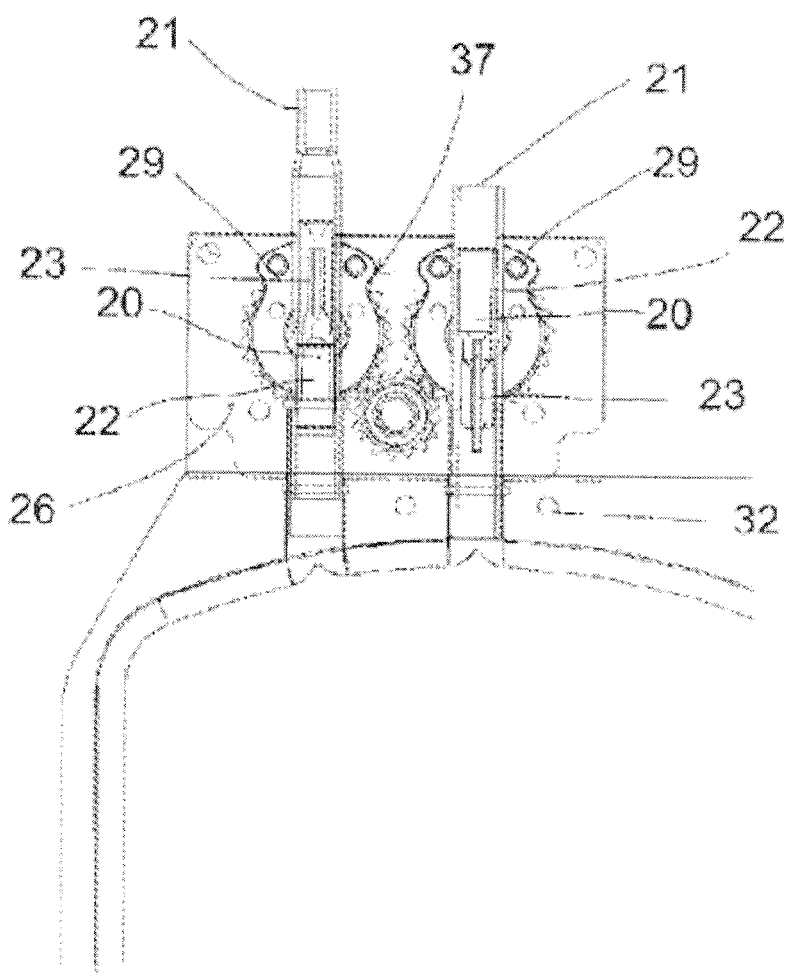
FIG. 9 shows another embodiment of the assembly as shown in FIG. 6.
Figure 10:
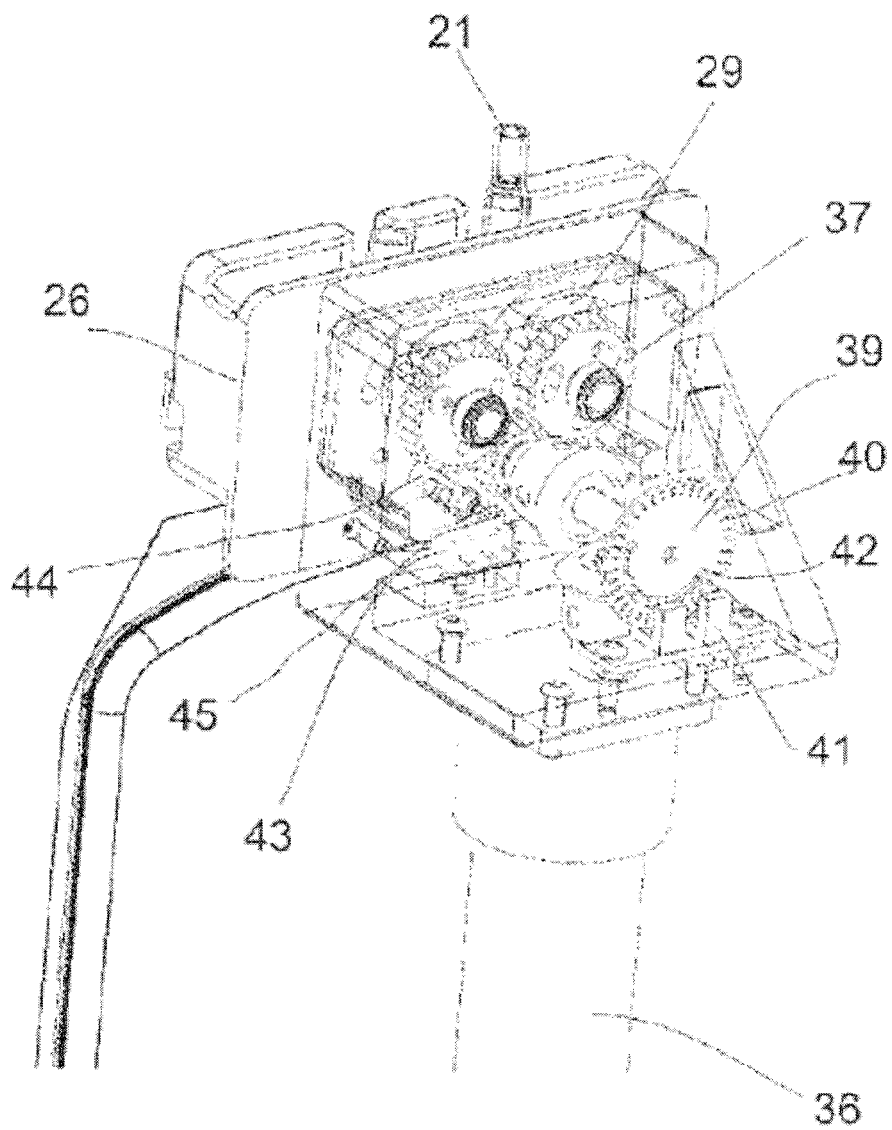
FIG. 10 shows a larger view of the assembly as shown in FIG. 9.

In the FIGS. 8 to 10, the member for moving 36 is for example a motor of which the drive shaft is made integral with the mobile element 29. A gear system 37 comprising at least two gears allow for the driving of said mobile element 29. The type of movement, linear or angular, is determined by the configuration of the gear system 37.

The motor is powered electrically, by batteries or directly by electric current via a power socket.

According to an alternative shown in FIGS. 9 and 10, the device is intended to break two closure elements 20, simultaneously or not.

To do this, the device can comprise another assembly for holding another flexible tube. This assembly for holding is similar to that just been described, with another fixed element and another mobile element, mounted on the member 36 which is arranged to move the mobile members 29 according to a rotational or linear movement (not shown). Alternatively, each mobile member 29 can be provided with its own member for moving.

However, when the device is intended to simultaneously break the two closure elements mounted in a flexible tube, respectively, it is advantageous to use only a single member for moving. As shown in the FIGS. 9 and 10, the mobile elements 29 are then mounted on said member for moving 36, in such a way as to simultaneously break the weakening zone of two closure elements 20. This embodiment is more compact and applies in particular to the simultaneous opening of two closure elements mounted in neighbouring flexible tubes forming orifices for accessing a flexible bag.

In this case, it is possible that the closure elements 20 be arranged in the opposite direction: for one of the closure elements, its base 22 is mounted closer to the bag and for the other element, the pen 23 is mounted closer to the bag (FIG. 9).

In normal use, the fixed element 27 is intended to hold the base 22 of the closure element 20 and the mobile element 29, the pen 23. However, the device also operates when the closure element 20 is placed in a reverse direction. In this case, it is the pen 23 which is housed in the fixed element 27 and the base 22 in the mobile element 29.

There are several types of closure elements on the market each having a specific configuration and dimensions. It is considered to manufacture assemblies for holding suitable for one or several types of closure elements in the form of a removable panel intended to be inserted into the gear system.

A control unit 38 makes it possible to control the operation of the device for breaking and in particular the actuating of the member 36 for moving the mobile element 29. The control unit 38 is for example a microprocessor mounted on a mother board.

In particular, the control unit operates and checks the operation of the member for moving 36 the device.

As shown in FIG. 10, the member for moving 36, such as the mobile element 29, is integral with a solid wheel 39 comprising a plurality of peripheral cavities 40. Alternatively, a gear is used. The rotation of this solid wheel 39 makes it possible to control the movement of the mobile element 29. In order to displace the mobile element 29, the member for moving rotates first in one direction during a determined number of cavities then in the other direction during another determined number of cavities. The number of cavities is calculated by the microprocessor based on the information received by a detector 41 placed on the cavities 40 of the wheel. The determined numbers of cavities correspond to the extreme positions of the mobile element 29.

Advantageously, the solid wheel 39 comprises another recess 42 in the shape of a half-circle concentric to the wheel 39 which makes it possible to determine the position of the mobile element 29. In the neutral or initial position of the mobile element 29, the wheel 39 is arranged in such a way that the detector 41 detects the interface between the semi-circular recess 42 and the solid.

In a particular example, the device comprises a means for detecting the presence of a flexible tube in the assembly for holding. In particular, a detector 43 of the presence of a flexible tube in at least one of the housings is provided. When the flexible tube 21 is inserted in one of the housings provided in the assembly for holding 26, a mobile rod 44 arranged in said housing pushes a tab 45 of a contactor of a detector which then emits a signal. This detector 43 of presence connected to the control unit advantageously prevents the operation of the device when no tube is arranged in the assembly for holding.

In another example, the device for breaking comprises a means for determining the energy used for breaking the weakening zone 24, for example by measuring the energy used by the member for moving 36. The current used by the motor to displace the mobile element is proportional to the force required to carry out the movement. This current is measured in order to detect the breakage of the closure element. As such, it is provided that the mobile element of the device for breaking continues its back-and-forth movement until the detection of a drop in the current revealing the complete breakage of the closure element.

All of the components of the device, including the assembly for holding, the member for moving, and the control unit are organised in a rigid case.

Various embodiments are considered for this device. A first embodiment consists in integrating this device into a portable tool. The device for breaking then comprises a handle. In particular, the device for breaking is used during the step of filtration the blood or one of its components, when the bag system is suspended from a stand, in order to initiate filtration. In FIG. 1, this device is used when the collection bag 2 is suspended from a stand in order to open the second closure element 17.

A second embodiment is a standalone module wherein this device is integrated. The user then arranges the closure elements in this device according to their need.

A third embodiment is a module directly integrated into an apparatus for treating a biological fluid such as blood. Indeed, it is conventional that the centrifugation and/or the separation be carried out by dedicated apparatuses, such as separators, centrifuges or presses such as those described in WO 2005/002644.

The integration of this device for breaking into blood treatment apparatuses facilitates the use of these apparatuses. The control unit is programmed to carry out the breaking of the closure elements according to a process determined in advance.

According to a second aspect of the invention, a method for breaking a closure element 20 using a device according to the first aspect shall now be described. The method comprises the steps of:
- placing the flexible tube 21 comprising the closure element 20 in the assembly for holding of said device with the weakening zone 24 arranged between the fixed element 27 and the mobile element 29,
- actuating the member 36 for moving the mobile element 29 on one side then the other of the centre line 31 in such a way as to break the weakening zone 24 of the closure element 20.

Advantageously, the first part 22 of the closure element is housed in the housing 28 of the fixed element 27 and the second part 23 of the closure element is housed in the housing 30 of the mobile element 29.

In order to break the weakening zone, one or several movements of the mobile element 29 on either side of the centre line 31 are carried out.

While the present invention has been particularly described, it is evident that many alternatives, modifications and variations will be apparent to those skilled in the art in light of the foregoing description. It is therefore contemplated that the appended claims will embrace any such alternatives, modifications, and variations as falling within the true scope and spirit of the present invention.

What is claimed is:

1. Device intended to break at least one closure element (20) arranged inside a flexible tube (21), said closure element (20) comprising a first part (22) and a second part (23) separated by a weakening zone (24), said weakening zone (24) able to be broken in order to enable fluid to flow inside said flexible tube (21), said device comprising an assembly for holding (26) said flexible tube (21), said assembly (26) comprising a fixed element (27) provided with a first housing (28) intended to hold a first portion of said flexible tube, and a mobile element (29) provided with a second housing (30) intended to hold a second portion of said flexible tube, the two housings (28,30) being aligned along a center line (31) defining a neutral position of the mobile element (29), said device being characterized in that it comprises a member (36) for moving the mobile element (29) to either side of a neutral position in such a way as to break the weakening zone (24) of the closure element (20) when the flexible tube (21) is placed in the assembly for holding (26).

2. Device according to claim 1, characterized in that it comprises another fixed element (27) and another mobile element (29), the member (36) being arranged to move the mobile members (29) in such a way as to simultaneous break the weakening zone (24) of two closure elements (20).

3. Device according to claim 2, characterized in that the mobile element (29) is driven in displacement according to a linear movement.

4. Device according to claim 2, characterized in that the mobile element (29) is driven in displacement according to a rotational movement.

5. Device according to claim 4, characterized in that the rotational movement is a movement of at least 30° on either side of the centre line (31).

6. Device according to claim 5, characterized in that the axis of rotation of the mobile element passes through the centre line (31).

7. Device according to claim 6, characterized in that at least one of the housings (28) is formed inside a U-shaped groove.

8. Device according to claim 7, characterized in that at least one of the housings (28) comprises a clamp (33) intended to tighten a portion of the flexible tube (21).

9. Device according to claim 8, characterized in that it comprises a means for detecting the presence of a flexible tube (21) in the assembly for holding (26).

10. Device according to claim 9, characterized in that it comprises a means for determining the energy used for the breaking of the weakening zone (24).

11. Device according to claim 10, characterized in that it comprises a handle.

12. Apparatus for treating a biological fluid comprising a flexible tube and a device, said device comprising:
   a closure element inside said flexible tube with a first part and a second part separated by a breakable weakening zone;
   an assembly for holding said flexible tube, said assembly comprising a fixed element with a first housing for holding a first portion of said flexible tube;
   a mobile element with a second housing for holding a second portion of said flexible tube;
   a member for moving the mobile element;
   a clamp;
   a handle;
   a means for detecting a presence of said flexible tube in said assembly;
   a means for determining an energy used for breaking of said weakening zone;
   wherein at least one of said first and second housings are formed inside a U-shaped groove;
   wherein said first and second housings are aligned along a center line defining a neutral position of said mobile element;
   wherein said member moves the mobile element to either side of said neutral position;
   wherein said movement of said mobile element breaks said weakening zone when said flexible tube is placed in said assembly; and
   wherein breaking said breakable weakening zone comprises enables a fluid to flow inside said flexible tube.

13. Method for breaking a closure element of an apparatus for treating biological fluid comprising the steps of:
   providing a device with a closure element having a first part and a second part, said device further comprising an assembly with a fixed element and a mobile element;
   providing a member for moving said mobile element;
   placing said closure elements inside a flexible tube;
   defining a weakening zone between said first part and said second part;
   placing said flexible tube (21) in said assembly for holding (26) said device with the weakening zone (24);
   actuating the member (36) for moving the mobile element (29) towards the right and towards the left in a back and forth movement passing through its neutral position, in such a way that the back and forth movement breaks the weakening zone (24) of the closure element (20).

14. Device according to claim 1, characterized in that the mobile element (29) is driven in displacement according to a rotational movement and an axis of rotation of the mobile element passes through the center line (31).

15. Device according to claim 1, characterized in that at least one of the housings (28) is formed inside a U-shaped groove.

16. Device according to claim 1, characterized in that at least one of the housings (28) comprises a clamp (33) intended to tighten a portion of the flexible tube (21).

17. Device according to claim 1, characterized in that it comprises a means for detecting the presence of a flexible tube (21) in the assembly for holding (26).

18. Device according to claim 1, characterized in that it comprises a means for determining the energy used for the breaking of the weakening zone (24).

19. Device according to claim 1, characterized in that it comprises a handle.

* * * * *